(12) United States Patent
Fisbein et al.

(10) Patent No.: US 9,089,733 B2
(45) Date of Patent: Jul. 28, 2015

(54) SYSTEMS AND METHODS FOR EXERCISE IN AN INTERACTIVE VIRTUAL ENVIRONMENT

(75) Inventors: Benjamin Fisbein, Brooklyn, NY (US); Sylvain Berlemont, Paris (FR)

(73) Assignee: BENAARON, LLC

( * ) Notice: Subject to any disclaimer, the term of this patent is extended or adjusted under 35 U.S.C. 154(b) by 184 days.

(21) Appl. No.: 13/880,338

(22) PCT Filed: Oct. 21, 2011

(86) PCT No.: PCT/US2011/057257
§ 371 (c)(1),
(2), (4) Date: Apr. 18, 2013

(87) PCT Pub. No.: WO2012/054818
PCT Pub. Date: Apr. 26, 2012

(65) Prior Publication Data
US 2013/0225369 A1    Aug. 29, 2013

Related U.S. Application Data

(60) Provisional application No. 61/405,366, filed on Oct. 21, 2010.

(51) Int. Cl.
*A63B 24/00* (2006.01)
*A63B 22/00* (2006.01)
(Continued)

(52) U.S. Cl.
CPC ............... *A63B 24/00* (2013.01); *A63B 22/00* (2013.01); *A63B 22/0242* (2013.01); *A63B 24/0062* (2013.01); *A63B 24/0075* (2013.01); *A63B 24/0087* (2013.01); *A63B 71/0622* (2013.01); *G06Q 30/02* (2013.01); *H04M 1/72522* (2013.01); *A63B 22/0056* (2013.01);
(Continued)

(58) Field of Classification Search
USPC ........................... 482/1–9, 900–902; 434/247
See application file for complete search history.

(56) References Cited

U.S. PATENT DOCUMENTS 5,205,800 A    4/1993    Grant
5,785,630 A    7/1998    Bobick et al.
(Continued)

FOREIGN PATENT DOCUMENTS

KR         10-0804190       2/2008
KR      10-2008-0073849     8/2008
(Continued)

OTHER PUBLICATIONS

Korean Intellectual Property Office, Written Opinion of the International Searching Authority, dated May 15, 2012, Republic of Korea.
(Continued)

*Primary Examiner* — Glenn Richman

(57) ABSTRACT

The present invention is directed to systems and processes for simulating exercise in an interactive virtual environment comprised of a minicomputer configured with course data from a course server to render a virtual environment on a coupled video display. The minicomputer is in communication with an exercise device via a translation interface such that interaction with the exercise device alters the rendered virtual environment. Additionally, the user may interact with the virtual environment via minicomputer input. An optional advertising server enables insertion of promotional material into the interactive virtual environment.

20 Claims, 7 Drawing Sheets

(51) Int. Cl.
*A63B 22/02* (2006.01)
*A63B 71/06* (2006.01)
*G06Q 30/02* (2012.01)
*H04M 1/725* (2006.01)
*G01S 19/19* (2010.01)

(52) U.S. Cl.
CPC ....... *A63B22/0076* (2013.01); *A63B 2024/009* (2013.01); *A63B 2071/0638* (2013.01); *A63B 2071/0647* (2013.01); *A63B 2220/12* (2013.01); *A63B 2220/30* (2013.01); *A63B 2220/40* (2013.01); *A63B 2225/20* (2013.01); *A63B 2225/50* (2013.01); *A63B 2225/685* (2013.01); *A63B 2230/06* (2013.01); *A63B 2230/062* (2013.01); *A63B 2230/30* (2013.01); *A63B 2230/50* (2013.01); *A63B 2230/75* (2013.01); *G01S 19/19* (2013.01); *H04M 1/72572* (2013.01)

(56) References Cited

U.S. PATENT DOCUMENTS

| | | | |
|---|---|---|---|
| 6,283,896 | B1 | 9/2001 | Grunfeld et al. |
| 6,616,578 | B2 | 9/2003 | Alessandri |
| 7,166,064 | B2 | 1/2007 | Watterson et al. |
| 7,465,257 | B1 | 12/2008 | Morgan, Jr. |
| 7,497,807 | B2 | 3/2009 | Neff et al. |
| 7,556,590 | B2 | 7/2009 | Watterson et al. |
| 7,628,730 | B1 | 12/2009 | Watterson et al. |
| 7,645,212 | B2 | 1/2010 | Ashby et al. |
| 7,695,406 | B2 | 4/2010 | Waters |
| 7,972,245 | B2 * | 7/2011 | Temple et al. ............ 482/8 |
| 8,579,632 | B2 * | 11/2013 | Crowley .................. 434/247 |
| 8,613,689 | B2 * | 12/2013 | Dyer et al. ............... 482/8 |
| 2002/0160883 | A1 | 10/2002 | Dugan |
| 2009/0210078 | A1 | 8/2009 | Crowley |
| 2009/0258710 | A1 | 10/2009 | Quatrochi |
| 2010/0125026 | A1 | 5/2010 | Zavadsky |

FOREIGN PATENT DOCUMENTS

| | | |
|---|---|---|
| KR | 10-0934009 | 12/2009 |
| KR | 10-0938922 | 1/2010 |
| WO | WO/94/16777 | 7/1994 |
| WO | WO/98/19746 | 5/1998 |
| WO | WO/02/101627 | 12/2002 |
| WO | WO/2005/004999 | 1/2005 |
| WO | WO/2006/103676 | 10/2006 |

OTHER PUBLICATIONS

Korean Intellectual Property Office, Written Opinion of International Searching Authority, May, 15, 2012, pp. 9-11, Republic of Korea.

* cited by examiner

SYSTEMS AND METHODS FOR EXERCISE IN AN INTERACTIVE VIRTUAL ENVIRONMENT

PRIORITY

The present invention claims priority to provisional application 61/405,366, which has a filing date of Oct. 21, 2010, which is hereby incorporated.

BACKGROUND

1. Field of the Invention

The present invention relates to systems and methods for interaction with exercise machines, more specifically to systems and methods for interaction with exercise machines in order to simulate interaction with a virtual environment.

2. Description of the Related Art

It's crucial to exercise to stay in good health and has become very popular in the last few years. Indoor exercise at places such as home, office, or the gymnasium using exercise devices is the exercise choice for many people. However, exercise can be boring and repetitive, resulting in a lack of motivation to maintain an exercise program. This leads to a sizable percentage of those people to terminate their exercise program.

Two key factors can support the long term maintenance of a vigorous indoor exercise program: group participation and sensory stimulation. Indoor exercise using an exercise machine is frequently performed alone. Even when exercise is performed in a group setting, there is no direct interaction in the workouts among the individuals in the group. Moreover indoor exercise is usually performed in the same place, therefore the lack of varying stimuli increases the repetitive and boring nature of a workout. Attempts to address the problems have included placing televisions in the workout space. Because the television programs don't have any connection or correlation to the exercise, that attempt is inadequate. Others have attempted to produce video synchronized to the exercise but that approach fails to immerse the user and fails to provide selectable, visual, real-time, interactive stimulation during the exercise program.

In addition to the barrier presented by the lack of stimulus during exercise, there is an economic practicality and barrier. Currently, gymnasiums have exercise equipment and video displays. They would prefer not purchase additional equipment that could not only be costly, but occupy similar physical space to that of flight simulators, especially at a time when a many users are adopting portable computing devices.

For the above reasons it would be advantageous to provide people who exercise with systems and processes for exercise that simulates interaction with a virtual environment using a minicomputer and an exercise machine.

SUMMARY

The present invention is directed to systems and processes for simulating exercise in an interactive virtual environment comprised of a minicomputer configured with course data from a course server to render a virtual environment on a coupled video display. The minicomputer is in communication with an exercise device via a translation interface such that interaction with the exercise device alters the rendered virtual environment. Additionally, the user may interact with the virtual environment via minicomputer input. An optional advertising server enables insertion of promotional material into the interactive virtual environment.

These and other features, aspects, and advantages of the invention will become better understood with reference to the following description, and accompanying drawings.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for claims and as a representative basis for teaching one skilled in the art to employ the present invention in virtually any appropriately detailed system, structure or manner.

Figure 1:
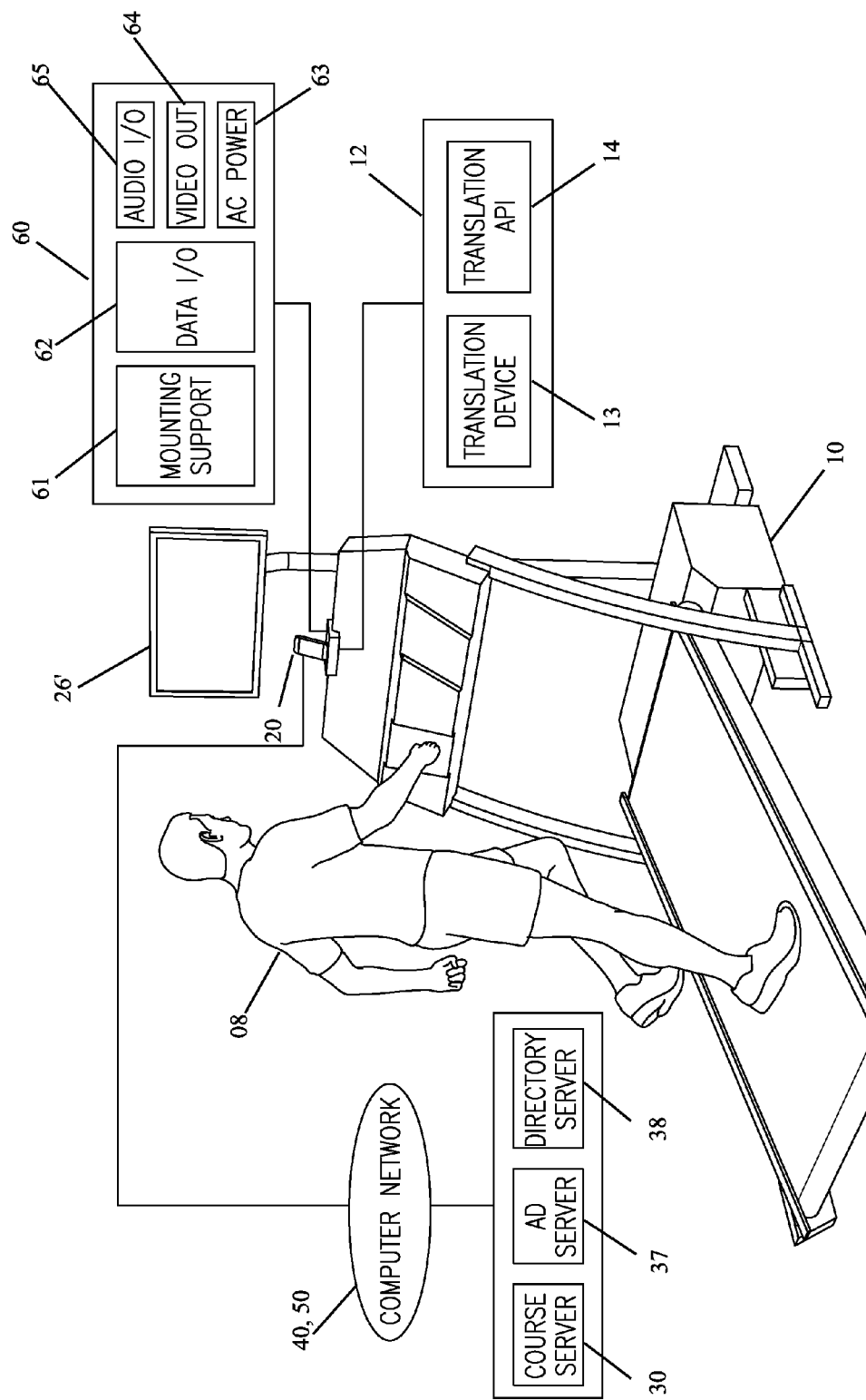
FIG. 1 illustrates an embodiment of a system according to the current invention.
Figure 2:
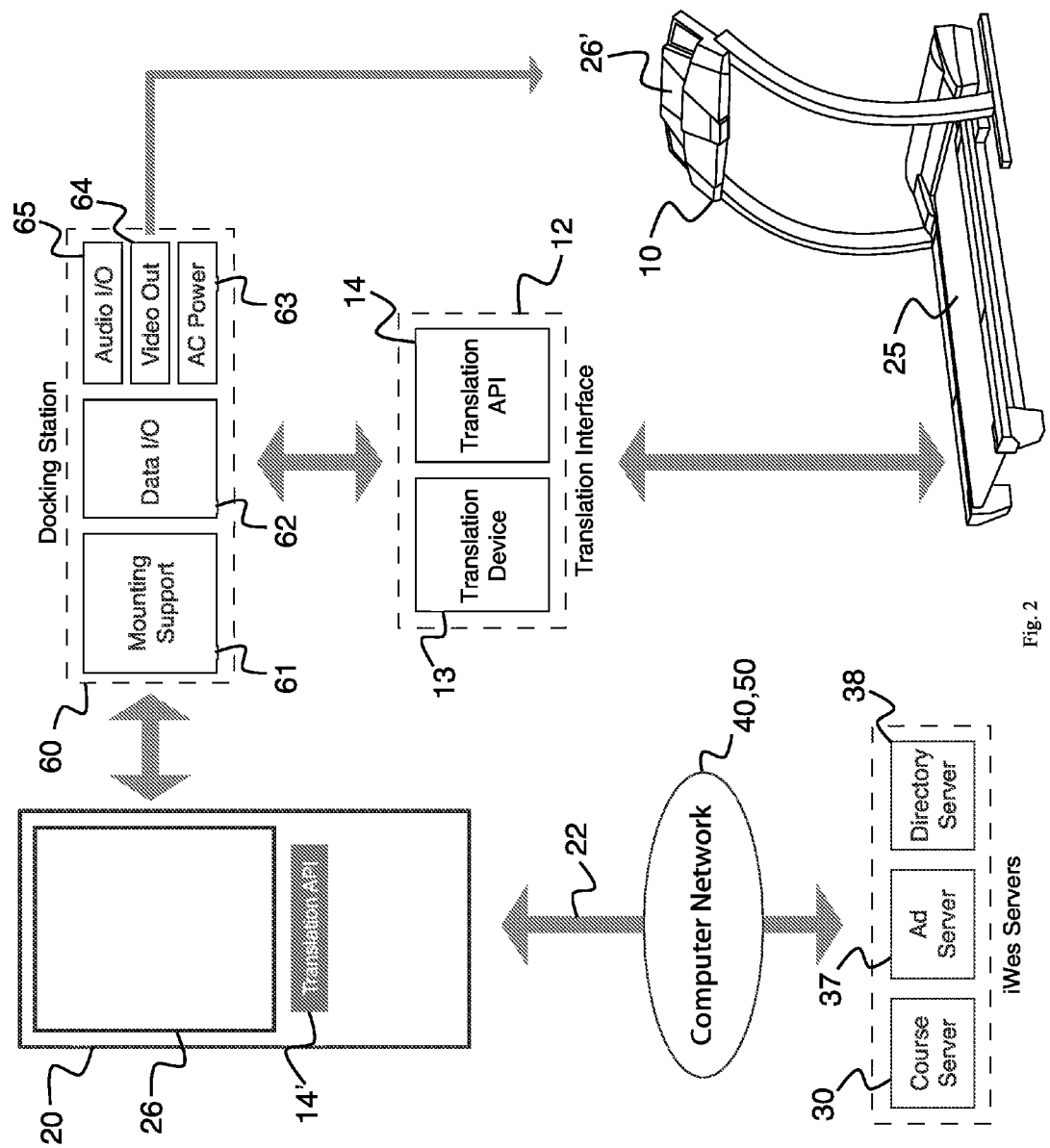
FIG. 2 illustrates a block diagram of an embodiment of FIG. 1.

The present invention relates to systems and methods for providing an interactive virtual environment to at least one user of an exercise machine 10. More specifically, an embodiment of the present invention employs real time bidirectional communication between an exercise machine 10, at least one minicomputer 20, and a course server 50, whereby the system renders an interactive virtual environment to a video display 26 26'. Optionally, the system includes an advertising server 37 for insertion of promotional material into the interactive virtual environment. Depicted in FIG. 1 is an embodiment of the current invention. Depicted in FIG. 2 is a block diagram of the embodiment depicted in FIG. 1. The depicted system includes an exercise machine 10, a minicomputer 20, communication network 40 50, and at least one server 30. As shown, an exercise device 10 bidirectionally communicates data with a minicomputer 20 via a translation interface 12. In turn, the minicomputer 20 renders an interactive virtual environment based on course data received from a course server 50. A plurality of exercise devices 10 coupled to minicomputers 20 can comprise a multiuser embodiment of the system.

Although each of the elements of system 10 are shown separated one from another, it may be appreciated by one skilled in the art that the hardware and/or software elements of the present invention can be incorporated together. For example, the functionality and/or the structure of translation interface 12 and/or minicomputer 20 may be partially or completely incorporated within respective exercises devices or mechanisms, such as the exercise device 10.

The depicted exercise device 10 is a treadmill, although stair steppers, ellipticals, striders, climbers, rowing machines, exercise cycle, ski machines, or any other device which is capable of simulating motion or transport may be employed. The preferred exercise device 10 includes manual user controls and an input for control signals. In addition to the ability to control and vary the speed of the belt, the depicted exercise device 10 also permits the degree of incline of the tread base to vary relative to the surface upon which the tread base rests. This can be accomplished through use of an incline drive motor that raises or lowers one end of the base relative to the other end.

The exercise device 10 includes memory to capture data regarding the exercise device 10 status and the user's 08 status. The exercise device 10 sensors may include magnets, speed sensors, solenoids, accelerometers, inclinometers, and other sensors to measure exercise parameters. The sensors enable monitoring of exercise device 10 conditions such as information relating to speed, resistance, incline, time, temperature, angular orientation, and other similar operating parameters and conditions. The exercise device 10 includes input and sensors to determine the user's condition. Examples of user data collected via such sensors or manual input include information relating to a user's age, weight, height, instantaneous pulse rate, low and high pulse rate, average pulse rate, calories expended, blood pressure, workout duration, total distance traveled, and other information specific to a user's exercise event.

The exercise machine 10 is implemented with an input/output protocol such as RS-232, USB, or Bluetooth. Embodiments of the present invention embrace the use of other transmission mediums for delivering and receiving data between an exercise device 10 and minicomputer 20, including a wireless communication system, a radio frequency (RF) communication system, fiber-optic communication system, and other communication systems capable of being used to transmit data as known by one skilled in the art. The exercise machine may be configured with the CSAFE or other low level protocols.

The sensor data, user data, and other data captured by the exercise device 10 is accessible by the minicomputer 20 in real time or delayed basis through a translation device 12. The translation interface 12 standardizes the output from the different exercise devices 10 for presentation to the minicomputer 20 and other elements of the system. Additionally, the translation interface 12 standardizes instructions from different minicomputers 20 for presentation of control signals to exercise devices 10.

A minicomputer 20, computer, or server 30 37 50 as referred to in this specification generally refers to a system which includes a central processing unit (CPU), memory, a screen, a network interface, and input/output (I/O) components connected by way of a data bus. The I/O components may include for example, a mouse, keyboard, buttons, or a touchscreen. The network interface enables data communications with the computer network 40. A server contains various server software programs and preferably contains application server software. The preferred minicomputer 20 is a smartphone or tablet PC dimensioned to fit in a pocket or carrying bag, such as iPhone, iPod Touch, iPad, Blackberry, or Android based device. The minicomputer may be configured with a global positioning system (GPS), touch screen, accelerometer, and/or integrated camera elements. Those skilled in the art will appreciate that minicomputer 20, servers 30 37 50 and/or translation interface 12 may take a variety of configurations, including personal computers, hand-held devices, multi-processor systems, microprocessor-based electronics, network PCs, minicomputers, mainframe computers, and the like. Additionally, minicomputer 20, servers 30 37 50, and/or translation interface 12 may be part of a distributed computer environment where tasks are performed by local and remote processing devices that are linked. Although shown as separate devices, one skilled in the art can understand that the structure of and functionality associated with the aforementioned elements can be optionally partially or completely incorporated within one or the other, such as within one or more processors.

During use of the system, the minicomputer 20 may rest in a dock station 60 and be secured to the exercise device 10 with a mounting support 61. The dock station 60 optionally includes a charger for the minicomputer 20, a video relay 64, and an audio relay 65. The video relay 64 contains a video input to receive a video signal from the minicomputer 20. The video signal can then be output a remote video display 26', which is coupled to the translation interface 12. The audio relay 65 contains an audio input to receive an audio signal from the minicomputer 20. The audio signal can then be relayed to an output such as a speaker or an audio input on the video display 26', which is coupled to the translation interface 12.

Figure 5:
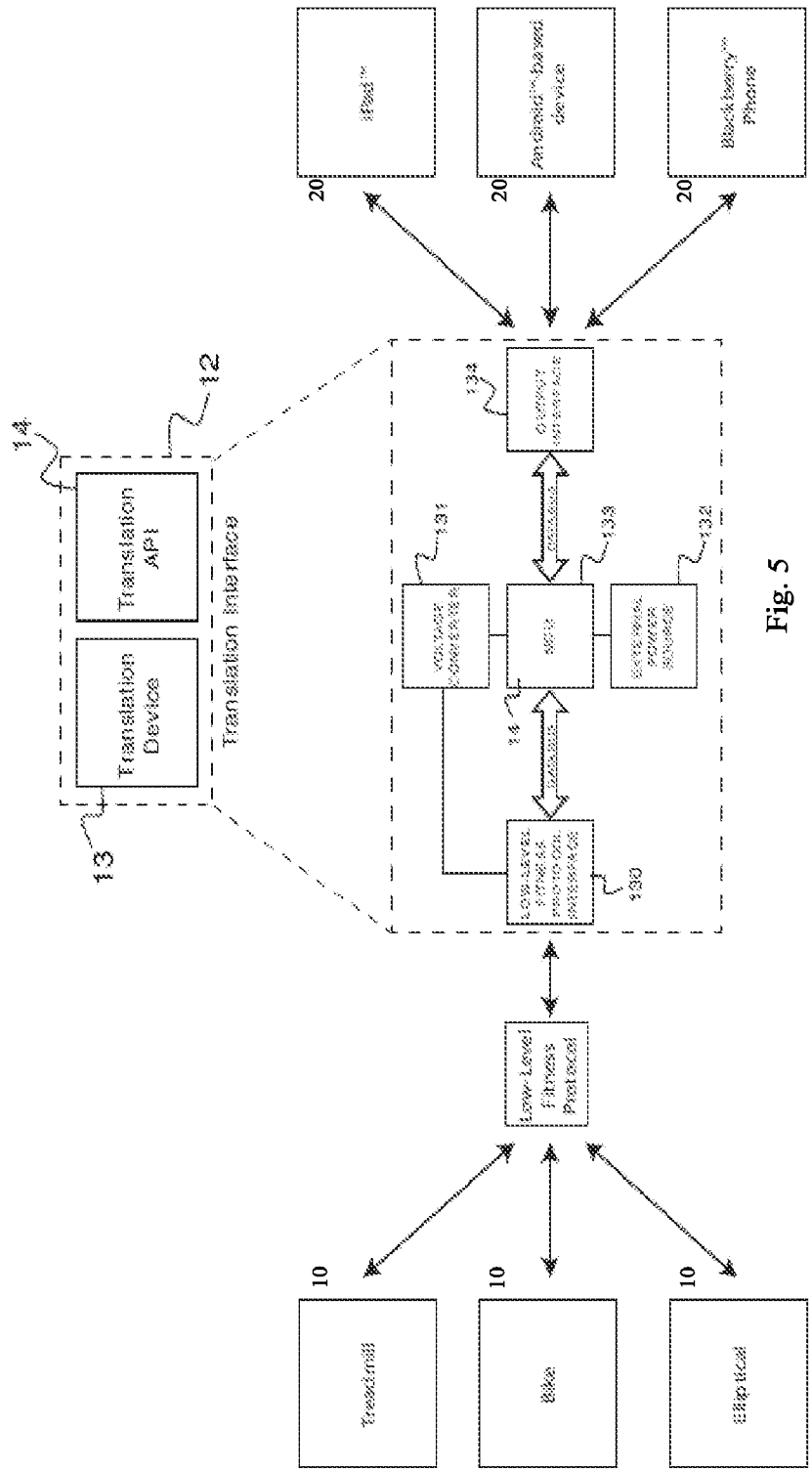
FIG. 5 illustrates state diagram of an embodiment a translation interface of FIG. 1.

As shown in FIG. 5, the translation interface 12 presents an electronic interface and a mechanical interface where necessary to enable varying exercise devices 10 to bidirectionally communicate with varying minicomputers 20 in order to enable interaction with the virtual environment defining the courses. When both the exercise device 10 and the minicomputer 20 are capable of wireless communication, no mechanical interface is presented. Otherwise, the mechanical interface presents two physical connections, one corresponding to the input/output connection of the exercise device 10 and another corresponding to the input/output connection of the minicomputer 20. Physical connectors include universal serial bus (USB), ethernet, serial, parallel, iPhone cables, and those known in the art.

The electronic interface presented by translation interface 12 resolves the communication between the exercise device 10 and the minicomputer 20 at the electrical layer and the data layer. The electronic interface resolves the necessary electrical signal characteristics necessary for the communication between the exercise device 10 and the minicomputer 20, such as voltage levels, signaling rate, and the like. The electronic interface also presents a translation application interface (API) 14 14' to standardize the bidirectional data and control signal communication. The translation API 14 14' is configured to translate the data between the protocol format of the minicomputer 20 and the protocol format of the exercise device 10 in order to enable and standardize communication between varying types of exercise devices 10 and varying types of minicomputers 20. The translation API 14 14' receives the response and translates the response into one that is formatted in accordance with the minicomputer 20 and the servers 30 37 50. The translation interface 12 and its associated elements 13 14' can be completely integrated with the minicomputer 20. Alternatively, the translation interface 12 and its associated elements 13 14 may be integrated with the dock station 60. In yet another alternative, elements of the dock station 60 or the translation interface 12 are integrated with the exercise device 10. In another configuration, the translation interface 12 is separate from the other elements of the system, enabling a user to couple a user supplied minicomputer 20 with a third party exercise device 10. The minicomputer 20 can communicate with the translation interface 12 via a physical or wireless connection. U.S. Pats. No. 7,556,590 and 7,695,406 contain additional disclosure on computer to exercise device interfaces and are hereby incorporated by reference.

Referring to FIG. 5, one configuration of a translation interface 12 is depicted. The translation interface 12 includes a controller 135 and at least two data buses 140 145. A first data bus 140 is a communication channel between the translation interface 12 and the exercise device 10. The physical connection can include an RJ-45 connection, RS-232 connection, USB plug, or similar connection, between the translation interface 12 and the exercise device 10. The controller 135 is implemented with an instruction set to communicate with the exercise device 10 using a low level fitness communication protocol, preferably the CSAFE specification.

A second data bus 145 is a communication channel between the translation interface 12 and the minicomputer 20. The communicate channel can occur over a wired interface, but preferably occurs over a wireless interface, such as Bluetooth or the Wifi 802.11 specification. The controller 135 is implemented with an instruction set to communicate with the minicomputer 20 of commonly available minicomputers, such as that of the iOs or Android operating system.

The translation interface presents a complete bidirectional communication channel between the exercise device 10 and the minicomputer 20. That is, signals can be communicated from the exercise device 10 to the minicomputer 20, with all necessary low level and application level translations occurring via the translation interface 12. A exercise device 10 may transmit a device specific output over the first data bus 140. The controller 135 processes, translates, and standardizes that output for presentation to the minicomputer 20 over the second data bus 145. In the other direction, a minicomputer 20 may transmit a generic instruction for the exercise device 10. The controller 135 processes, translates, and standardizes that generic instruction to present a device specific control signal. The communication between the translation interface 12 and the minicomputer 20 is preferably wireless over Bluetooth or WiFi 802.x protocol.

The preferred minicomputer 20 has an integrated video display 26 but may also be coupled to an external video display 26'. The video display, whether integrated or external, is preferably touch sensitive for user interaction with the virtual environment. The preferred minicomputer 20 has an integrated microphone but may also be coupled to an external microphone. The minicomputer 20 has an audio output to broadcast audio to an integrated speaker, an external speaker, a course server 30, or the telephone system 50.

The communication network 22 includes a computer network 40 and a telephone system 50. The computer network 40 includes of a variety of network components and protocols known in the art which enable computers to communicate. The computer network may be a local area network or wide area network such as the internet. The network may include modem lines, high speed dedicated lines, packet switches, etc. The network protocols used may include those known in the art such as UDP, TCP, IP, IPX, or the like. Additional communication protocols may be used to facilitate communication over the computer network 40, such as the published HTTP protocol used on the world wide web or other application protocols.

The telephone system 50 is the circuit-switched telephone network worldwide network of telephone lines, fiber optic cables, microwave transmission links, cellular networks, communications satellites, and undersea telephone cables connected by switching centers, which allows any telephone in the world to communicate with any other. More specifically, it includes a system capable of digital transmission of data over the telephone system 50 and routing data to and from the computer network 40 such as 3G, 4G, LTE, and WiMax.

The user directory server 38 hosts the user directory which in turn contains user profiles of people in the system. An individual who does not have an existing profile in the user directory 38 can be invited to create an account by another user, an administrator, or the system before using the system. An individual may register on a minicomputer 20 or directly on the user directory server 38. The individual is presented with an interface to enter data such as name, contact information, e-mail address, location (for example, city and country), age, sex, height, weight, health conditions, interests, exercise club memberships, social media membership, website memberships, desired travel destinations, fitness plans and goals, and an avatar. The system can aid or supplement the input using sources such as the minicomputer's GPS or third-party application data via APIs, or cookies. The system retrievably stores the user data in the user directory 38.

The course server 30 is one or more computers which control, direct, and respond to the communication traffic with the minicomputers 20. Additionally, the course server 30 control and direct request for course data. Where a minicomputer 20 requests a course, or a subset thereof, the course server 30 transmits the course data to the minicomputer 20. Where multiple users simultaneously enter a single interactive virtual environment, the course server 30 relays and optionally processes course information, such as position data, from each user's minicomputer 20 to support multiuser interaction in the virtual environment.

The course server also controls, directs, and responds with the advertisement server 37 and the user directory server 40.

The course server 30 hosts the course directory, which includes the available courses. Each course uses geospatial or geospatially derived data as the base data. Supplemental data is added to the base data to complete the data set representing an interactive virtual environment available to users of the system. The geospatial data may be accurate geospatial data for a real locale, geospatial data derived from a real locale, or geospatial data for a purely fictional location. A course may contain complete geospatial data set for the represented region. Alternatively, a course may only include geospatial data for a set path through the represented region and visual data for the remainder of the region in order to alter the size and throughput potential for the data set. The geospatial data is preferably based on the shapefile format by Environmental Systems Research Institute but can use alternate formats such as Open Geospatial Consortium, ARC Digitized Raster Graphics, Compressed ARC Digitised Raster Graphics, AutoCAD DXF format, Cartesian coordinate system, National Geospatial-Intelligence Agency Digital Terrain Elevation Data, or other formats depending on the geographical location, desired resolution, processing requirements, storage requirements, and the like.

Figure 4:
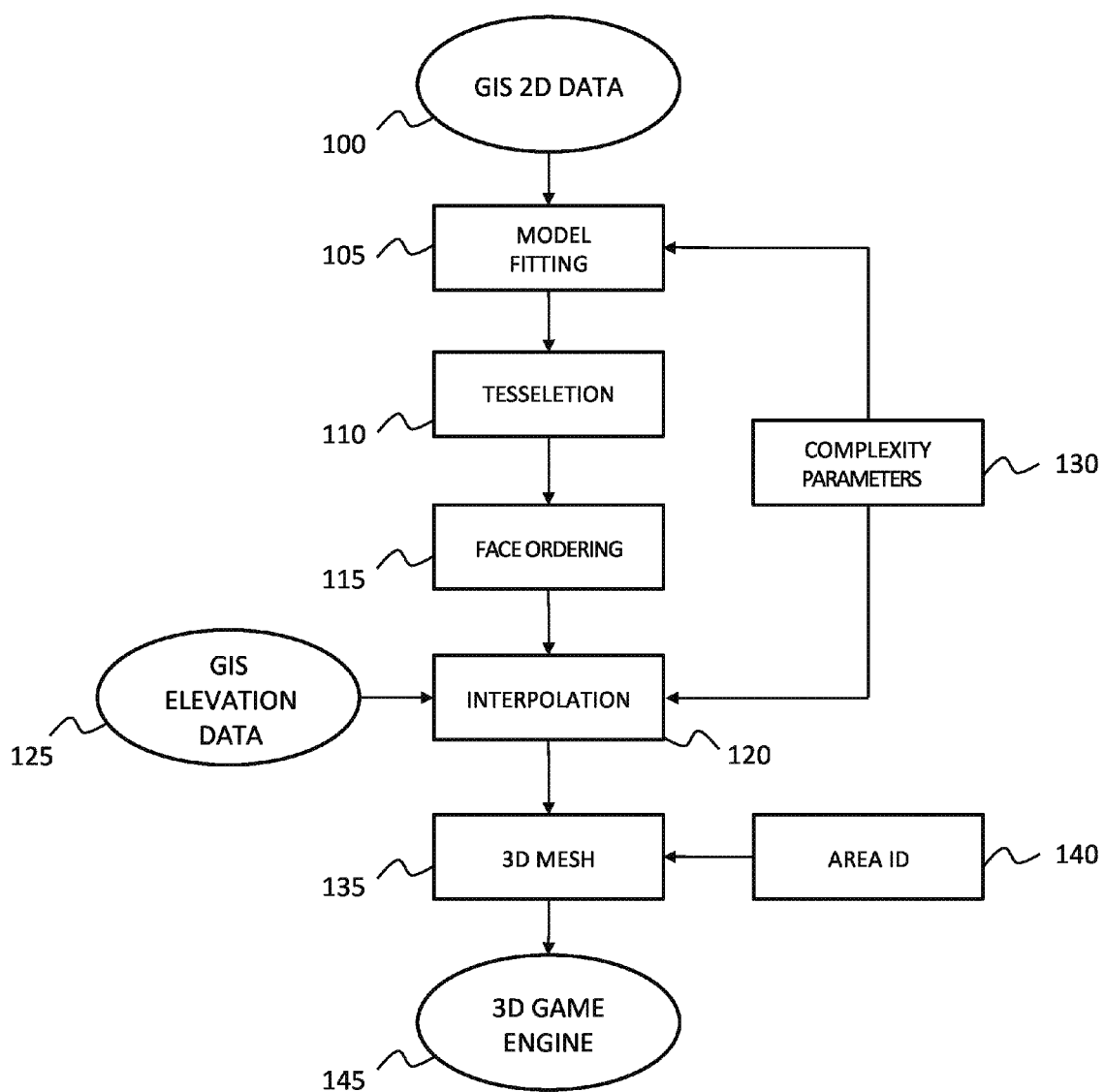
FIG. 4 illustrates a workflow used to create an interactive virtual environment.
Figure 6:
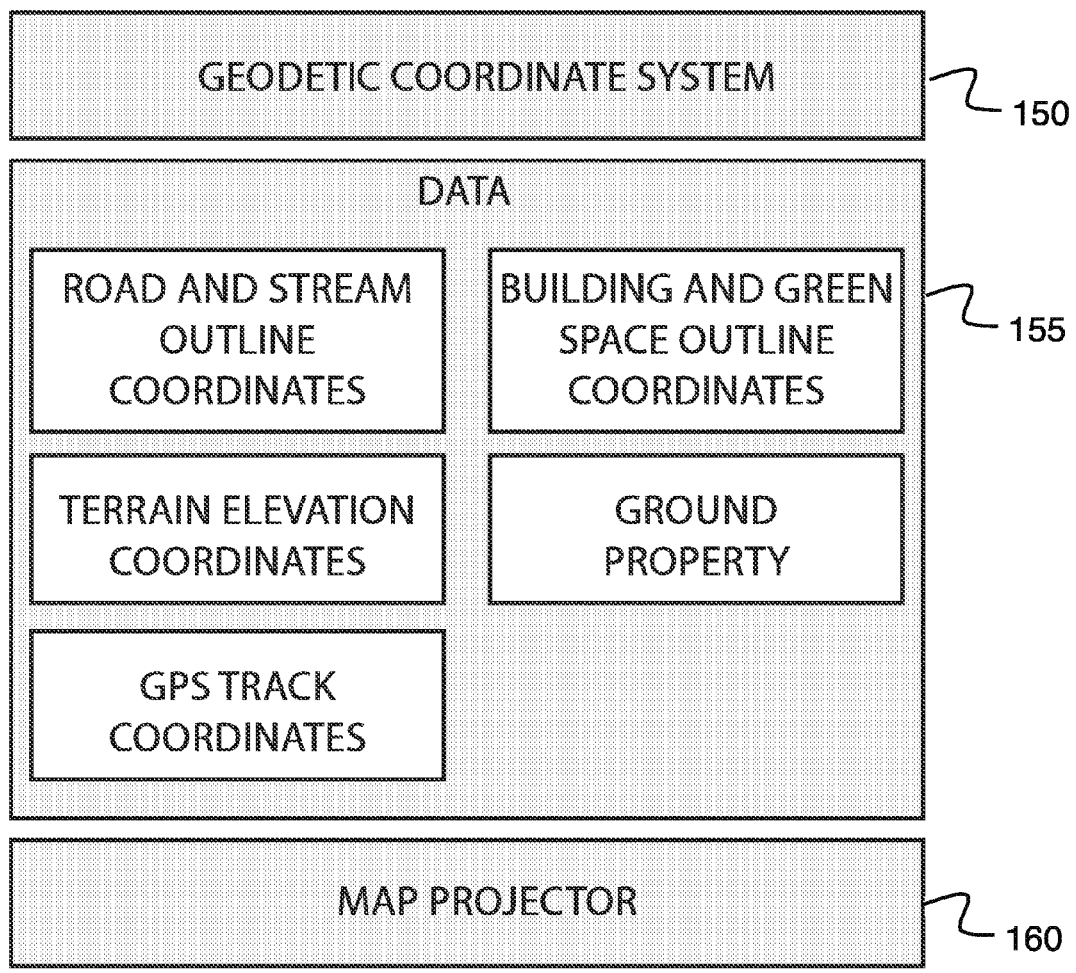
FIG. 6 illustrates representative input data to the process of FIG. 4.

The course data is preferably preprocessed from the base format to optimize performance factors such as data size, network throughput, minicomputer 20 processing, anticipated network latencies, and similar factors. Referring to FIG. 4, a representative workflow of creating an interactive virtual environment from the base geospatial data is depicted. High-resolution 2-dimensional measures such as roads, building outlines, outdoors areas and water outlines are provided as input 100. FIG. 6 shows representative input. GIS data represents full or partial components of geographic information about real places. This data is made of 3 components: a coordinate system 150, the data set 155, and eventually a map projector system 160. The data set is usually described in a computerized format consisting of either vectorial information like points, line segments or curves, or rasterized information, such as aerial images. This information can described various environment elements such as road and stream, terrain elevation, building and green space and so on. Outlines of such elements are usually described as point sets, polygons and smooth curves. Coordinates are usually expressed in a standard geodetic coordinate system 150.

Example of such system is NAD83 or WGS84. A coordinate in such system represents a point on the Earth. This point needs to be projected on a plane to be used in applications such as a procedural 3D terrain design like the one depicted in FIG. 4. Projection is performed using various projector systems such as the Lambert Conformal Conic projection.

Figure 7:
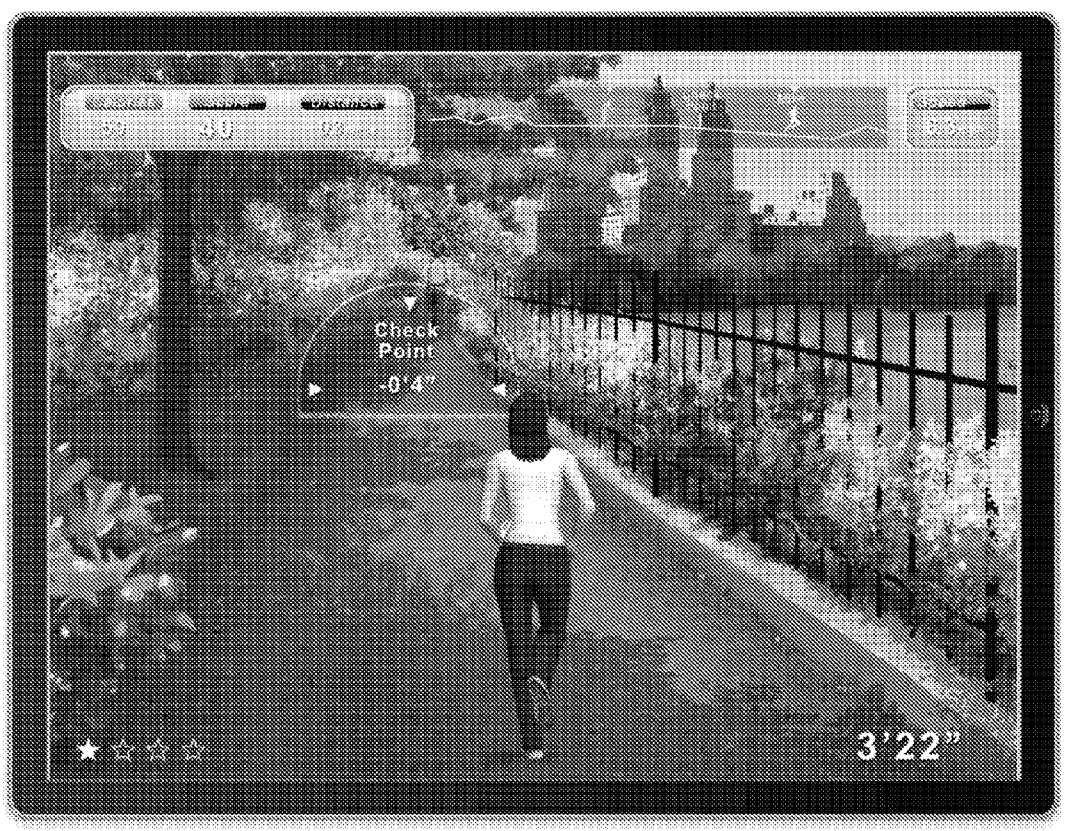
FIG. 7 illustrates representative output data to the process of FIG. 4.

Referring back to FIG. 4, the raw data of FIG. 6 consisting of set of line segments, points and polygons is processed 105 in order to reach an expected level of complexity defined by an input parameter 130. This step encompasses processes such as, but not limited to, shape simplification, curve smoothing using B-spline interpolations, or polygons merging. Points defining the above 2-dimensional elements are then linked together using tessellation triangulation 110. This process yields a list of 2-dimensional triangles, which are then reorganized to enable fast rendering of triangular strips 115. Then, low-resolution height map, such as 3-30 meter resolution maps provided by the National Elevation Dataset (NED), as well as high precision scattered points are combined together to produce a uniform grid of terrain elevation values 125. High precision scattered points can be obtained by altimeter measurements or similar procedures. A complexity parameter is calculated to control the size of the grid mesh 130. Using bilinear or bicubic interpolation 120, an elevation value is assigned to each 2-dimensional vertex of a triangle calculated from step 110 to produce the final 3D terrain mesh 135. A color or texture is then assigned to triangles whether they are part of a road, an outdoor water area, or other types of terrain. FIG. 7 shows a representative visual depiction of a portion a course. Additional information on transforming data using this process and alternative processes for transforming data into a format useful for simulated interaction is disclosed in U.S. Pat. Nos. 7,286,708, 7,254,271, RE40,693, 7,583,275, 7,101,284, 6,380,952 and U.S. Pat. Apps. Nos. 20080065359 and 20040105573, which are incorporated by reference.

Figure 3:
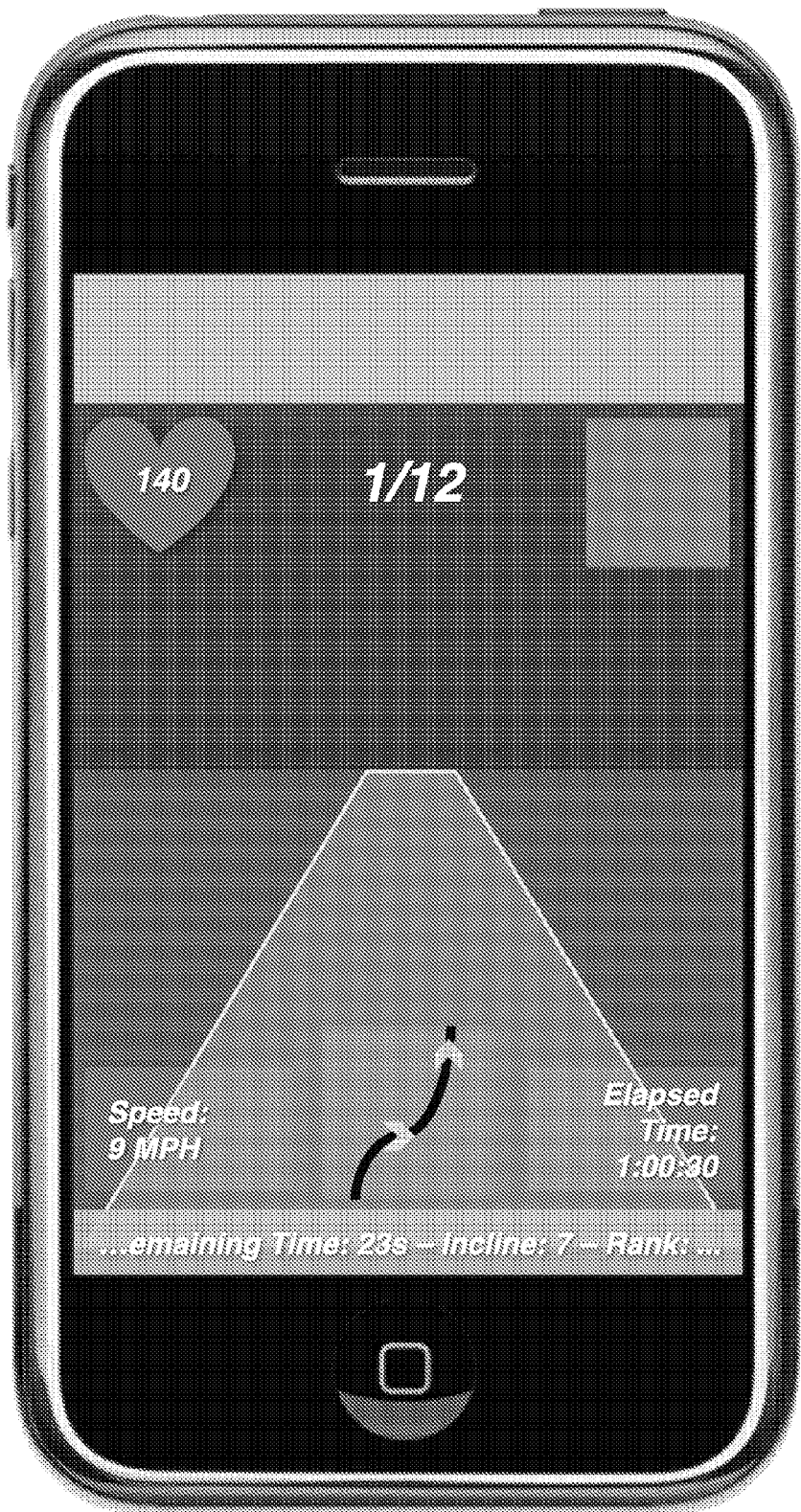
FIG. 3 illustrates a video display of the embodiment of FIG. 1.

With the minicomputer 20 in communication with the course server 30 and the exercise device 10, the foundation is presented for integration of the exercise experience with the interactive virtual environment. Referring now to FIG. 3 is a representation of a minicomputer 20 illustrating an interactive virtual environment to the user on the video display 26 26'. As the user engages the exercise device 10, simulated motion in the interactive virtual environment responsive to the output from the exercise device 10 occurs. As the user exercises, the translation interface 12 receives data from the exercise device 10, such as speed, incremental distance, or other updates from the exercise device 10. The translation interface 12 standardizes the exercise device 10 output and relays the output to minicomputer 20. The minicomputer 20 transmits the data to the course server 30, which calculates the user's new position and orientation in the interactive virtual environment based on the transmitted data. The updated position and orientation in the interactive virtual environment is communicated back to the minicomputer 20 and the updated position is rendered on the video display 26 26'. The updated video data for rendering the interactive virtual environment is preferably processed on the minicomputer 20, but optionally some or all of the processing may occur on the course server 30. The resultant video data is transmitted and displayed on the video display 26 26'.

The geospatial data representative of each course defining each interactive virtual environment can include course conditions or characteristics. The course and characteristics are simulated on the exercise device 10. The minicomputer 20 transmits instructions to the translation interface 12, which in turn transmits device specific control signals to the exercise device 10 according to the course data. These control signals vary one or more operating parameters of the exercise device 10 as the user traverses a course. The control signals change one or more operating parameters of the exercise device in response to the course data, such as the speed, incline, difficulty of exercise program, and the like of an exercise program. For instance, when the user reaches an incline or decline in the course defining the interactive virtual environment, the device specific control signals received by the exercise device will cause the exercise device 10, in the case of a treadmill, to vary the inclination or declination of the tread base in accordance with the virtual inclination or declination of the course. In the case of an exercise bike, the resistance may increase or decrease in accordance with the virtual inclination or declination of the course. It should be understood that not all exercise devices 10 will have control signals for full manipulation of the interactive virtual environment. In such cases, the control can be supplemented from the minicomputer. For example, a basic treadmill may only emulate motion on a single axis. For full engagement and interact with a course, a user may need to view the environment off the direction of the user's travel (change perspective) or the user may need to simulate a change in direction (a turn) in order to remain on the exercise path in the interactive virtual environment. Where a treadmill may not accept control signals for turns, the user may engage the touchscreen of the video display to "turn" in the interactive virtual environment. Thus the user may engage the touchscreen to see different perspectives of the interactive virtual environment. It should also be understood that the device specific control signals vary according to the capability and configuration of the exercise device 10. For instance, a where the exercise device 10 is an exercise cycle, an interactive virtual environment with sand or a similar surface would lead to the system initiating a control signal to the exercise device 10 to increase resistance to the exercise device 10 of that user. On the other hand, a treadmill emulates walking, thus sand would not have such a significant frictional resistance. In such a case, the system may not transmit any control signals to the exercise device 10 or the calculated difference in simulated resistance may lead to transmittal of a control signal increasing resistance by a minimal percentage. The system adjusts the resistance and other configurable parameters of the exercise device 10 according to the terrain of the simulated environment.

The prior discussion was directed to only a single exercise device 10, however, it may be appreciated that a similar discussion may be made for the illustrated configuration that includes multiple exercise devices. A plurality of users may exist in the same interactive virtual environment for companionship or competition. The position of each user is communicated across the communication network 22 and updated periodically to allow for a display in each user's video display 26 26'. Each user can view a likeness of the other users in the same interactive virtual environment when the users are in virtual proximity. A protocol 22 is implemented in the system to maintain communication and continuity in the interactive virtual environment of each user. The minicomputer 20 of each user preferably communicates real-time user event data or exercise device 10 data such as location, direction, speed, pulse, start and end race notifications, and game clock to the servers 30 37 38. The protocol 22 is optimized for such factors as underlying system capacity, network latency, number of users, and geographical distances between users and the servers 30 37 38. Thus the servers 30 37 38 may completely process or partially process the data before distributing the resultant multiuser data to other minicomputers 20. Alternatively, the servers 30 37 38 may distribute unprocessed data for later processing by the minicomputer 20 of each user to determine the resulting multiuser data in the simulated environment.

Additionally, the users may communicate over an audio channel on either a real time basis via the computer network 40 or the telephone system 50. Users can enter the interactive virtual environment with different exercise devices 10, on the same exercise device 10 one after another, combinations thereof, or the like. Once all of the users have completed the course, each can exit the interactive virtual environment and view performance statistics.

Still referring to FIG. 3, the video display 26 26' can also show the user status, such as the user's current pulse rate overlying the interactive virtual environment, to maintain an appropriate workout for the user and/or to alert the user prior entering into an unhealthy or hazardous pulse rate.

Optionally, the system includes an advertisement server 37 in communication with the course server 30. The advertisement server hosts promotional content for third-party goods and services for integration into the interactive virtual environment. The promotional content may be initially displayed in the manner as it customarily exists in a non-virtual environment. Thus the promotional content may be rendered on objects such as on billboards, benches, buildings, vehicles, and the like. A user is able to engage that promotional content by touching the promotional content. Upon user engagement of the promotional content, the promotion content is preferably optimized for user viewing while maintaining the exercise session. For example, the promotional content's apparent placement, angular orientation, and dimensions may be altered from it's original apparent position so that it continually appears in front of the user in the interactive virtual environment as the user's simulated position changes. The promotional content may be presented to the user as semi-transparent interactive banner style ads which are sufficiently transparent such that the user can maintain his view of the underlying interactive virtual environment. The user can further interact with the promotional content via the touchscreen or other input device. The user is presented options to view associated promotional content, such as videos, or subscribe to additional information from the provider of the goods or services. The user can also engage the promotional content to indicate the preference to no longer view the promotional content from a particular provider. If the user does not engage the promotional content, the system will remove it after a configurable period of time.

The system display advertisements based on the user's profile, the statistics from the user's workout data, interactive virtual environment locales. For example, where a user chooses an interactive virtual environment based on a real location, the system may present advertisements for travel to that destination. For instance, where the user competes at the upper percentile of a category, the user may be presented with specialized sports apparatus.

To use the system, the user engages the minicomputer 20 to the exercise device 10 and the external video display 26'. The minicomputer 20 establishes a connection with the exercise device 20. The user then selects an interactive virtual environment from the available courses. The selected course is retrieved from the course server 30, if necessary. Optionally, the user can solicit other users in the user directory 40 to join in the interactive virtual environment. The system may assist the user selection by using the minicomputer's 20 GPS, user profile information, or other system data. The users start to exercise on their respective exercise devices 10 and the interactive virtual environment and user status is rendered and updated on the video display 26 26' for each user as is shown in FIG. 3. Upon completion of the course, all users' exercise data and statistics, such as the type of exercise, users participating, path taken, distance traveled, and ranking, are displayed and retrievably stored. The exercise data and statistics are stored in the user directory 40 enabling the users of the system to additionally compete against a previously stored event.

Insofar as the description above and the accompanying drawing disclose any additional subject matter that is not within the scope of the single claim below, the inventions are not dedicated to the public and the right to file one or more applications to claim such additional inventions is reserved.

What is claimed is:

1. An exercise system comprising:
an exercise machine, a translation interface, a minicomputer, a display, and a course server;
said course server embedded with course data, said course data comprised of geospatial data supplemented with corresponding visual data;
said course server communicatively coupled to said minicomputer;
said minicomputer communicatively coupled to said translation interface;
said translation interface disposed between said minicomputer and said exercise machine, said translation interface further comprised of a translation device and a translation API; said translation device enabling electronic communication with said exercise machine and said translation API standardizing communication between said minicomputer and said exercise machine;
whereby a virtual environment is rendered to said display in response to real-time output from said exercise machine.

2. The system of claim 1 wherein said real-time output from said exercise machine includes velocity data.

3. The system of claim 1 wherein said real-time output from said exercise machine includes resistance data.

4. The system of claim 1 wherein said real-time output from said exercise machine includes inclination data.

5. The system of claim 1 wherein said real-time output from said exercise machine includes user data.

6. The system of claim 1 wherein the system generates real-time device specific control signals according to the configurable parameters of said exercise machine and according to said course data.

7. The system of claim 1 wherein said virtual environment is rendered responsive to user input to the minicomputer.

8. The system of claim 1 wherein said translation interface is configured with a low level fitness protocol.

9. The system of claim 1 wherein said translation interface is configured with the CSAFE protocol.

10. The system of claim 1 wherein said course data incorporates media from an advertisement server.

11. A device configured to enable exercise in a virtual environment comprising:
a translation interface disposed between a minicomputer and an exercise machine; said translation interface comprised of a translation device and a translation API;
said translation device enabling electronic communication with said exercise machine and said translation API standardizing communication between said minicomputer and said exercise machine;
said translation interface operable to receive real-time output from said exercise machine and to relay said output to said minicomputer;
said translation interface operable to generate control signals to said exercise machine in response to received information from said course, whereby said translation interface enables rendering a virtual environment based on user input and said exercise machine output.

12. The device of claim 11 further comprising a video output.

13. The device of claim 11 further comprising an audio output.

14. The device of claim 11 wherein said translation interface is configured with a low level device protocol.

15. The device of claim 11 wherein said translation interface is configured with the CSAFE protocol.

16. The device of claim 11 further comprising a power input, said input adapted to receive electrical energy from a port of said exercise device.

17. The device of claim 11 wherein said translation interface further comprises a radio operable to wirelessly communicate with said minicomputer.

18. An exercise system comprising:
a translation interface and a course server;
said course server embedded with course data, said course data comprised of geospatial data supplemented with corresponding visual data;
said course server having a communication channel for bidirectional communication with a minicomputer;
said translation interface enabled for communication between said minicomputer and an exercise machine;
said translation interface further comprised of a translation device and a translation API;
said translation device enabling electronic communication between said exercise machine and said minicomputer via said translation API standardizing communication between said minicomputer and said exercise machine;
whereby a virtual environment is rendered to a display in response to real-time communication among said exercise machine, said translation device, and said minicomputer.

19. The system of claim 18 wherein said real-time communication from the exercise machine is selected from group velocity data, resistance data, and inclination data.

20. The system of claim 18, wherein said translation interface further comprises a power input, said power input adapted to receive electrical energy from a port of said exercise device.

* * * * *